(12) United States Patent
Wheeler et al.

(10) Patent No.: US 7,824,034 B2
(45) Date of Patent: Nov. 2, 2010

(54) IRIS IMAGING SYSTEM AND METHOD FOR THE SAME

(75) Inventors: Frederick Wilson Wheeler, Niskayuna, NY (US); Siavash Yazdanfar, Niskayuna, NY (US)

(73) Assignee: UTC Fire & Security Americas Corporation, Inc., Bradenton, FL (US)

( * ) Notice: Subject to any disclaimer, the term of this patent is extended or adjusted under 35 U.S.C. 154(b) by 0 days.

(21) Appl. No.: 11/857,581

(22) Filed: Sep. 19, 2007

(65) Prior Publication Data

US 2009/0073381 A1 Mar. 19, 2009

(51) Int. Cl.
- *A61B 3/14* (2006.01)
- *A61B 3/00* (2006.01)
- *A61B 3/10* (2006.01)

(52) U.S. Cl. .................. 351/206; 351/200; 351/221

(58) Field of Classification Search .................. 351/200, 351/205–206, 208, 210, 221
See application file for complete search history.

(56) References Cited

U.S. PATENT DOCUMENTS

| | | | |
|---|---|---|---|
| 4,641,349 A | 2/1987 | Flom et al. | |
| 5,291,560 A | 3/1994 | Daugman | |
| 5,572,596 A | 11/1996 | Wildes et al. | |
| 6,247,813 B1 * | 6/2001 | Kim et al. | 351/206 |
| 6,542,624 B1 * | 4/2003 | Oda | 382/117 |
| 6,832,044 B2 | 12/2004 | Doi et al. | |
| 6,975,232 B1 * | 12/2005 | McKenna | 340/573.1 |
| 7,091,845 B2 | 8/2006 | Midland et al. | |
| 2006/0072793 A1 | 4/2006 | Determan | |

* cited by examiner

Primary Examiner—Scott J Sugarman
Assistant Examiner—Dawayne A Pinkney
(74) Attorney, Agent, or Firm—Armstrong Teasdale LLP

(57) ABSTRACT

An iris imaging system is provided. The iris imaging system includes at least one light source configured to illuminate an iris at a spectrum of light. The iris imaging system also includes at least one image capturing device including at least one of an indium-gallium-arsenide, lead sulphide, and lead selenide based detector and configured to capture an image of the iris via light reflected from the iris at the spectrum. The device is further configured to provide a signal representing one or more features of the iris in response to the light reflected from the iris.

23 Claims, 6 Drawing Sheets

IRIS IMAGING SYSTEM AND METHOD FOR THE SAME

BACKGROUND

The invention relates generally to security systems, and more particularly to biometric identification systems.

The human iris is commonly used as a biometric identifier in security systems due to high recognition rates, negligible false recognition rates, and contactless collection. Iris imaging is typically done using illumination with a spectrum centered around 800 nm. The spectrum of light used is restricted by the sensitivity of the detector. Typically, Silicon-based detectors are used, which have reduced sensitivity above 900 nm and negligible sensitivity above 1000 nm. A disadvantage to using illumination at these wavelengths is that the amount of illumination must be limited to protect the human eye from damage. Accordingly, since the level of illumination is diminished, a subject must be at a short distance, i.e., about one foot, from an image capturing device to capture an iris image of desirable quality for identification without the use of particularly sensitive cameras. Further, some eye colors do not lend themselves to easy image capture. For example, while blue eyes are generally easier to capture iris images of, brown eyes are not.

It is desirable to image the iris from longer distances such as, for example, about three meters. Further, in current iris imaging systems, the subject has to pause and hold his/her face close to the image capturing device, and obtaining a good image often requires user training and feedback from the imaging systems. Rapid iris image collection with minimal cooperation or delay as the subject walks past a biometric identification checkpoint will enable more applications of iris imaging systems. In addition, imaging the iris from longer distances requires usage of expensive image capturing devices and poses technical challenges.

Therefore, an improved iris imaging system is desirable to address one or more of the aforementioned issues.

BRIEF DESCRIPTION

In accordance with an embodiment of the invention, an iris imaging system is provided. The iris imaging system includes at least one light source configured to illuminate an iris with a spectrum of light. The iris imaging system also includes at least one image capturing device including at least one of an indium-gallium-arsenide, lead sulphide and lead selenide based detector and configured to capture an image of the iris via light reflected from the iris at the spectrum. The device is further configured to provide a signal representing one or more features of the iris in response to the light reflected from the iris.

In accordance with another embodiment of the invention, an iris imaging system including at least one light source configured to illuminate an iris at a spectrum of light greater than about 1000 nm is provided. The iris imaging system also includes at least one image capturing device including a detector and configured to capture an image of the iris via light reflected from the iris at the spectrum. The device is further configured to provide a signal representing one or more features of the iris in response to the light reflected from the iris.

In accordance with another embodiment of the invention, a method of fabricating an iris imaging system is provided. The method includes providing at least one light source for illuminating an iris with a spectrum of light. The method also includes providing an image capturing device including an indium-gallium-arsenide detector for capturing an image of the iris and for providing a signal representing one or more features of the iris.

In accordance with another embodiment of the invention, another method of fabricating an iris imaging system is provided. The method includes providing at least one light source for illuminating an iris with a spectrum of light. The method also includes providing an image capturing device configured to illuminate the iris at a spectrum greater than about 1000 nm for capturing an image of the iris and for providing a signal representing one or more features of the iris.

These and other advantages and features will be more readily understood from the following detailed description of preferred embodiments of the invention that is provided in connection with the accompanying drawings.

DRAWINGS

DETAILED DESCRIPTION

Embodiments of the invention are directed toward an iris imaging system and a method for manufacturing the same. As used herein, the term 'iris' refers to a muscle within an eye that regulates the size of a pupil and controls the amount of light entering the eye.

Figure 1:
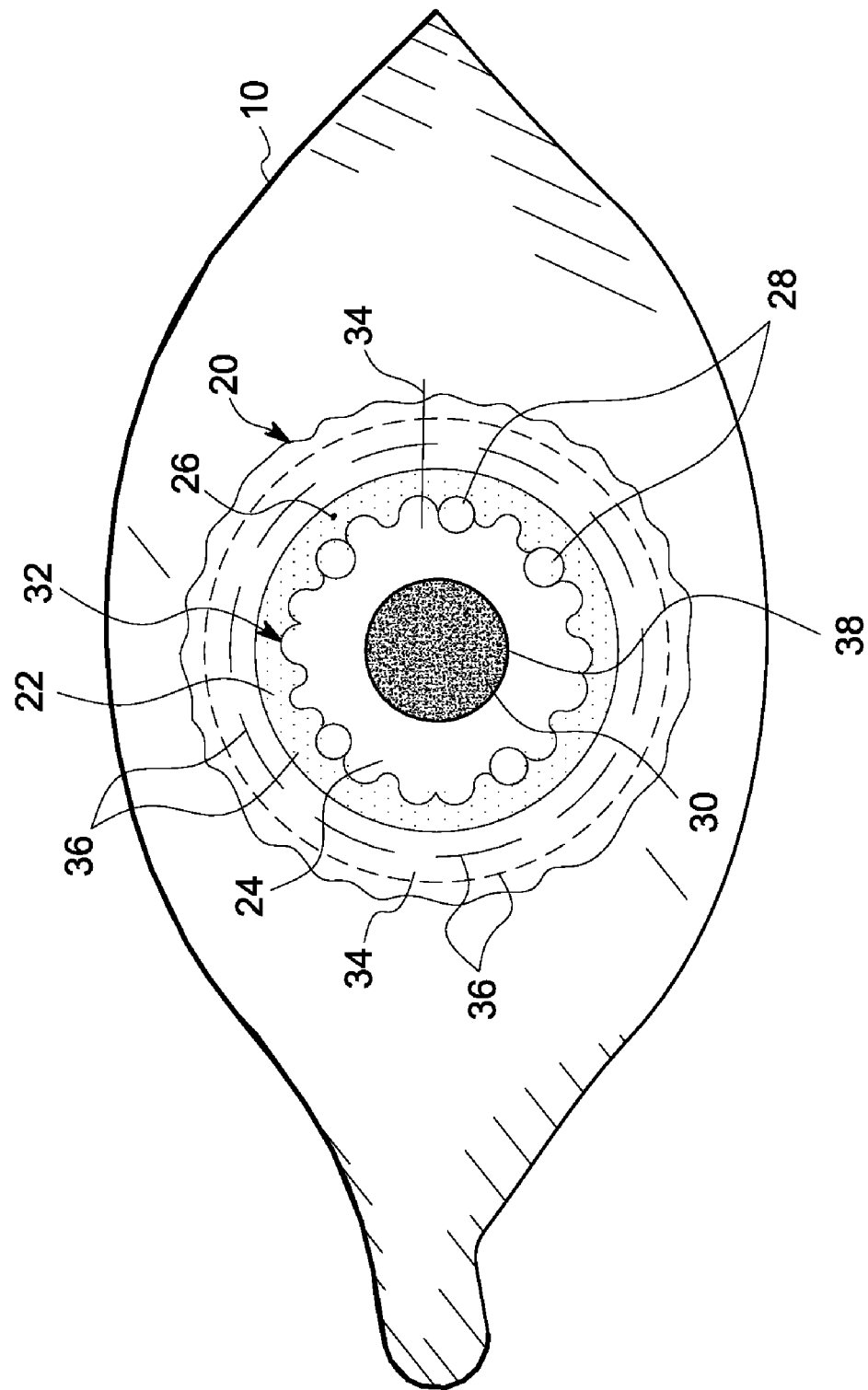
FIG. 1 is a schematic view of an iris and a pupil of an eye.

FIG. 1 is a simplified drawing of an eye 10, showing in detail the features of an iris 20 and a pupil 30. The eye 10 as illustrated is a human eye, but is applicable to some animals have a similar eye structure, permitting identification by the systems and method of the invention. The pupil 30 is a black, light receptive orifice, while iris 20 may have any of a broad range of hues and may be irregularly pigmented. The iris 20 and pupil 30 are closely related in function. A non-limiting example of a function of the iris 20 includes controlling the size of the pupil 30. Therefore, in addition to the visible features of the iris 20 relating to pigmentation, a number of visible features relate to the movements made by iris 20 in order to contract and dilate pupil 30. The iris 20 may be divided into a ciliary area 22, which is an annular region at its periphery, and a pupillary area 24, which is an annular area bordering pupil 30. When an illumination enters the pupil 30 and falls on a retina of the eye 10, a tissue of the iris 20 that is soft and loosely woven, controls muscles within the iris 20 causing the size of the pupil 30 to grow larger or smaller to regulate the amount of light entering the pupil 30. The change in the size of the pupil 30 results from involuntary reflexes and is not under conscious control.

Among the pigment-related features of the iris 20 are pigment spots 26. Some non-limiting types of the pigment spots 26 are moles, freckles, and nevi. The pigment spots 26 are random concentrations of pigment-bearing cells in a visible surface of the iris 20, and generally appear in the ciliary area 22. Crypts 28, unlike pigment spots 26, relate both to pigmentation and to a surface structure of the iris 20.

In addition to the pigment-related features of the iris 20, several other visible features relate to a function of controlling the size of the pupil 30. Collarette 32, is a boundary between the ciliary area 22 and the pupillary area 24, and is typically a sinuous line, which forms an elevated ridge running roughly parallel with the margin of the pupil 30. The collarette 32 is the thickest part of the iris 20.

Extending radially in relation to the center of pupil 30 are radial furrows 34. A typical radial furrow 34 may begin near pupil 30 and extend through collarette 32. Radial furrows 34 are creases in an anterior layer of the iris 20, from which loose tissue may bulge outward, and it is this loose tissue which permits the iris 20 to expand or contract, changing the size of pupil 30. Similarly, concentric furrows 36 are creases from which loose tissue may bulge outward, but their shape is generally circular and concentric with the pupil, so that they permit expansion and contraction of the iris in a different direction than the radial furrows 34. The concentric furrows 36 typically appear in the ciliary area 22, near the periphery of iris 20.

A most striking visible feature of eye 10 is typically the pupil 30. It should be appreciated that the pupil 30 may not be exactly circular in shape, as illustrated in FIG. 1, and its deviation from a circle is a visible characteristic. A pigment frill 38 at a margin of the pupil 30 is a protruding portion of a posterior layer of the iris 20 and typically has a very dark brown color.

As discussed in detail below, embodiments of the invention are based on imaging the iris 20 of the eye 10 for identification. It has been observed that an iris 20 is unique for each person, even the eyes 10 of identical twins. Furthermore, the iris 20 of each eye 10 of any person is different from that of his other eye 10. Moreover, although specific details of an appearance of the iris 20 may vary dramatically over time, depending on level and direction of illumination, the basic, significant features of the iris 20 remain extremely stable and do not change over a period of many years.

Figure 2:
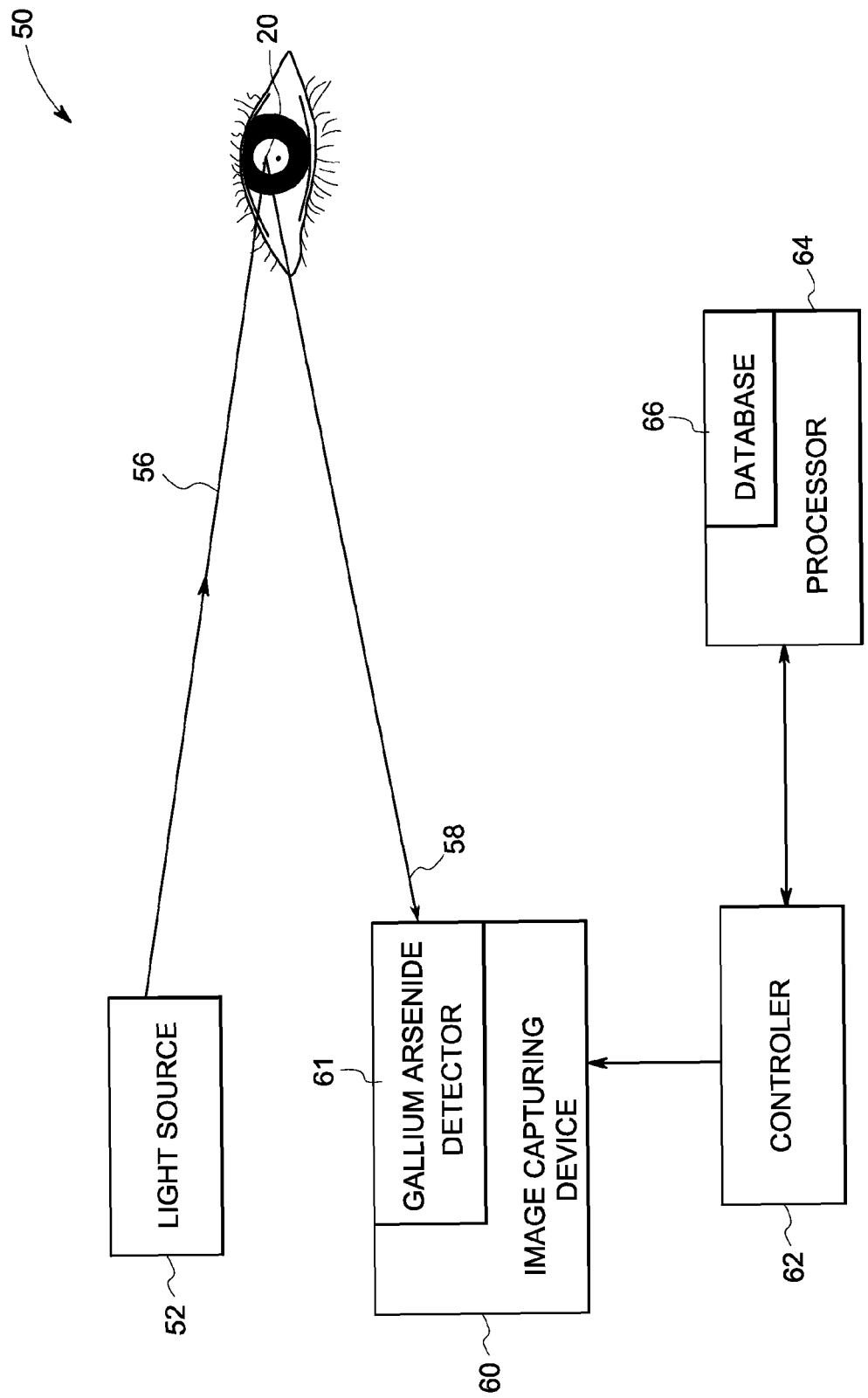
FIG. 2 is a schematic illustration of an iris imaging system in accordance with an embodiment of the invention.

Referring to FIG. 2, there is shown an exemplary iris imaging system 50. The iris imaging system 50 includes at least one light source 52 that illuminates an iris, such as the iris 20 of FIG. 1, at a spectrum of light 56. In one embodiment, the light source 52 comprises an infrared spectrum. In another embodiment, the light source 52 is configured to illuminate at about 1300 nm. In yet another embodiment, the light source 52 is configured to illuminate at about 1550 nm. As used herein, the term 'about' refers to a fractional bandwidth of 15%. In one example, the bandwidth covers illumination from 1203 nm to 1398 nm at 1300 nm. In another example, the bandwidth covers illumination from 1434 nm to about 1666 nm at 1550 nm. In another exemplary embodiment, the light source 52 is configured to illuminate at about 1650 nm. In another embodiment, the light source 52 is a broadband source.

In another exemplary embodiment, the at least one light source 52 (FIG. 2) illuminates the iris 20 at a spectrum greater than about 1000 nm. Further, the image capturing device 60 includes a detector and captures an image of the iris 20 via the reflected beam 58 at the spectrum of light greater than about 1000 nm. In one embodiment, the light source 52 includes a bandwidth that ranges between about 1300 nm and about 1550 nm. In another embodiment, the image capturing device 60 is configured to capture an image of the iris 20 at about 1300 nm. In yet another embodiment, the image capturing device 60 is configured to capture an image of the iris 20 at about 1550 nm.

Light 56 from the light source 52 that becomes incident on the iris 20 is reflected from the iris 20, resulting in a reflected beam 58 that is captured by an image capturing device 60. In a particular embodiment, the image capturing device 60 is a camera. The reflected beam 58 includes one or more features of the iris 20. The device 60 provides a signal representing the one or more features of the iris 20 embedded in the reflected beam 58 for localization and identification purposes. The image capturing device 60 may include at least one of an indium-gallium-arsenide (InGaAs), lead sulphide, and a lead selenide based detector 61. A controller 62 controls movement of the image capturing device 60. A processor 64 performs a localization of the iris 20 using the signal representing one or more features of the iris 20 provided by the device 60. As used herein, the term "localization" refers to a process wherein the iris 20 is located or characterized using the features obtained from the signal. The localization enables the processor 64 to compare the features of the iris 20 with a database 66 of multiple iris patterns. The iris 20 is further recognized based upon the comparison.

Figure 3:
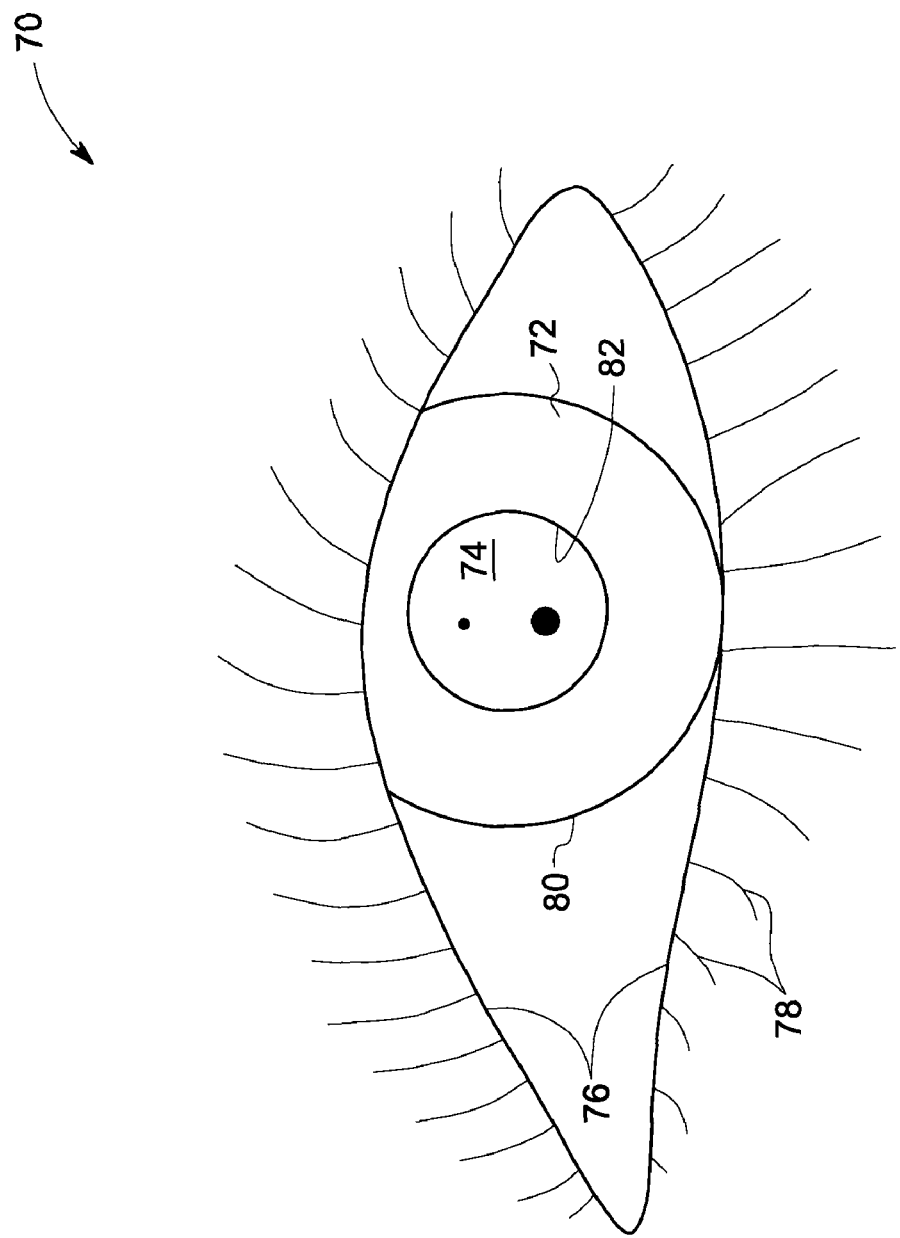
FIG. 3 is an illustration of a localized iris in accordance with an embodiment of the invention.

FIG. 3 is an illustration of an eye 70 including an exemplary localized iris 72 surrounding a pupil 74. The localized iris 72 is defined by locating boundary lines 76 for eyelids 78, an outline 80 for the iris 72 and an outline 82 for the pupil 74. The outline 82 may also be referred to as a pupillary boundary. In one embodiment, the boundary lines 76 for the eyelids 78 may not be determined or used. The localization of the iris 72 is critical to ensure that identical portions of the iris 72 are assigned identical coordinates every time an image is analyzed, regardless of degree of pupillary dilation. Upon imaging of the iris 20 (FIG. 2), an effective strategy for extracting textural information from images, such as detailed patterns of the iris 20, may be performed with multiple quadrature bandpass filters. In a non-limiting example, a two-dimensional Gabor wavelet filter is used. The bandpass filters map different segments of the iris 20 into phasors or vectors. The phasors include information on orientation, spatial frequency and position of the segments of the iris 20. The information is used to map an iris code of the iris 20.

Figure 4:
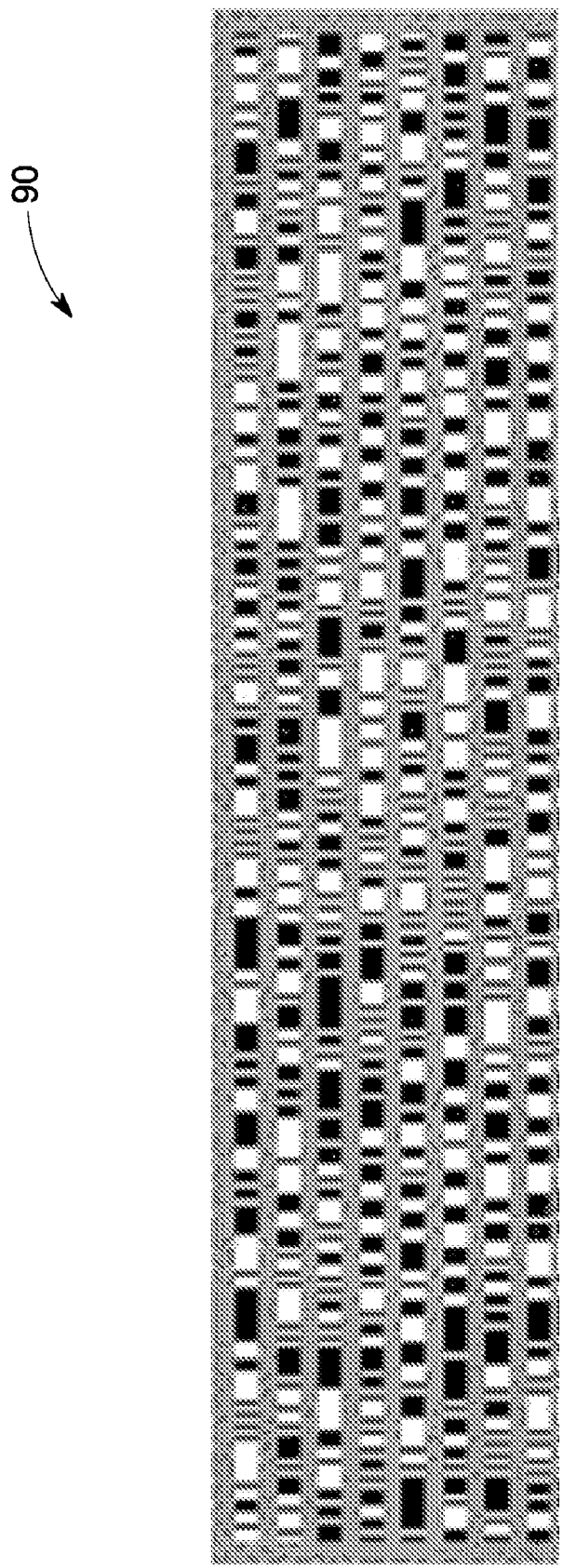
FIG. 4 is a diagrammatic illustration of an exemplary iris code.

FIG. 4 is a diagrammatic illustration of an exemplary iris code 90. In a particular embodiment, the iris code 90 includes a series of bits, or 0 and 1 values. A first iris code generated of an iris 20 (FIG. 2) is stored as a reference code. The reference code is used for comparison and identification of the iris 20 upon subsequent encounters with a person. A presented code obtained upon a subsequent encounter is compared to the reference code to obtain a Hamming distance. The Hamming distance permits the processor 64 (FIG. 2) to establish, confirm, or disconfirm an identity of the person, and to calculate a confidence level for a decision made.

It should be noted that embodiments of the invention are not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

Figure 5:
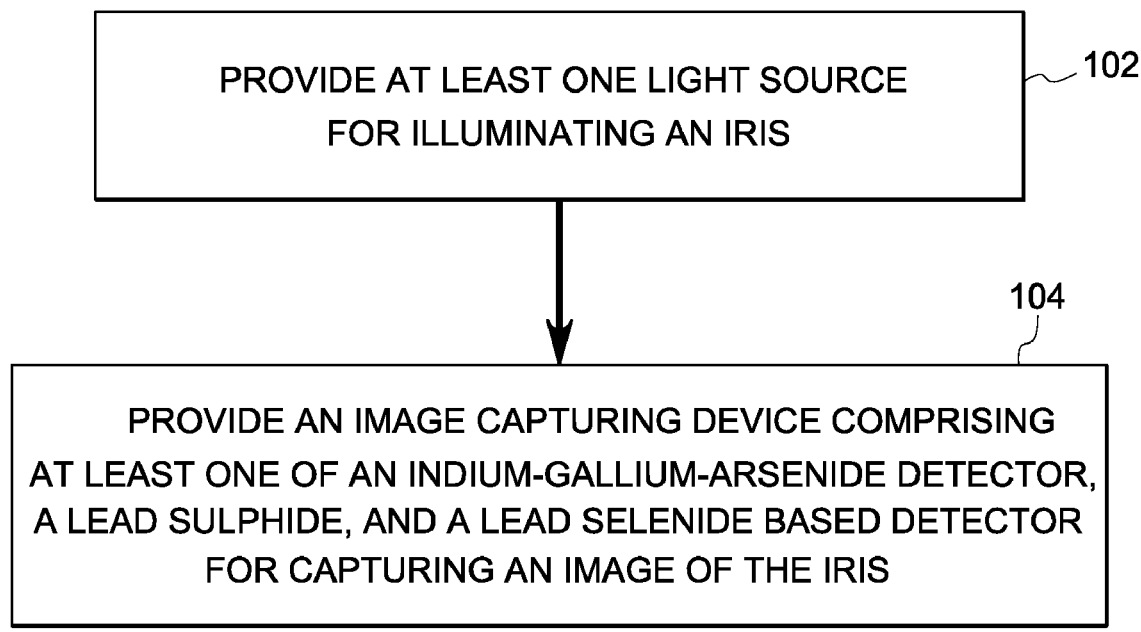
FIG. 5 is a flow chart representing steps in a method for fabricating an iris imaging system in accordance with an embodiment of the invention.

FIG. 5 is a flow chart representing steps in an exemplary method for fabricating an iris imaging system. The method includes providing at least one light source for illuminating an iris with a spectrum of light in step 102. An image capturing device including at least one of an indium-gallium-arsenide, a lead sulphide and a lead selenide based detector captures an image of the iris and provides a signal representing one or more features of the iris in step 104. In a particular embodiment, the image capturing device is mounted on one or more fixed or pan-tilt mounts. In another embodiment, a processor performs localization of the iris using features of the iris and comparison of the features of the iris with a database of iris patterns. Furthermore, the processor performs the iris recognition based upon the comparison.

Figure 6:
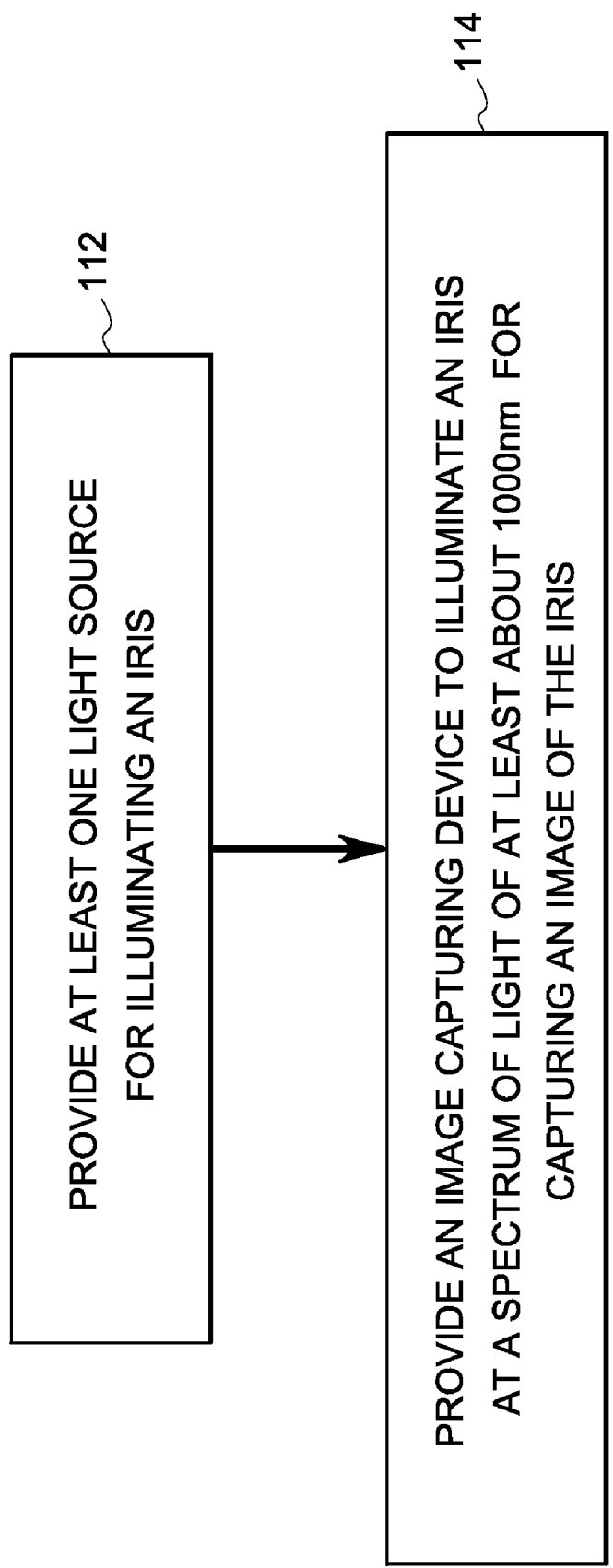
FIG. 6 is a flow chart representing steps in another method for fabricating an iris imaging system in accordance with an embodiment of the invention.

FIG. 6 is a flow chart representing steps in another exemplary method for fabricating an iris imaging system. The method includes providing at least one light source for illuminating an iris with a spectrum of light in step 112. An image capturing device illuminates the iris at a spectrum of light of at least about 1000 nm for capturing an image of the iris and provides a signal representing one or more features of the iris in step 114. In a particular embodiment, the image capturing device is mounted on one or more fixed or pan-tilt mounts. In another embodiment, a processor performs localization of the iris using features of the iris and comparison of the features of the iris with a database of iris patterns. Furthermore, the processor performs the iris recognition based upon the comparison.

The various embodiments of an iris imaging system and method described above thus provide a way to achieve a convenient and efficient biometric identification for security applications. The spectrum of light at which the iris is illuminated also enables imaging of the iris at greater distances than that is currently used. Further, the system and technique allows for safer and cost effective security means.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of an indium-gallium-arsenide detector with respect to one embodiment can be adapted for use with a camera configured to capture an image at a spectrum of light of at least about 1000 nm described with respect to another. Similarly, the various features described, as well as other known equivalents for each feature, can be mixed and matched by one of ordinary skill in this art to construct additional systems and techniques in accordance with principles of this disclosure.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. An iris imaging system, comprising:
   at least one light source configured to illuminate an iris with a spectrum of light; and
   at least one image capturing device comprising at least one of an indium-gallium-arsenide, a lead sulphide and a lead selenide based detector, the at least one image capturing device configured to:
   capture an image of the iris via light reflected from the iris at the spectrum; and
   provide a signal representing one or more features of the iris in response to the light reflected from the iris.

2. The system of claim 1, comprising a controller configured to control movement of the image capturing device.

3. The system of claim 1, comprising a processor configured to:
   localize the iris using the signal representing one or more features of the iris;
   compare the features with a database of a plurality of iris patterns; and
   recognize the iris based upon the comparison.

4. The system of claim 1, wherein the image capturing device comprises a camera.

5. The system of claim 1, wherein the spectrum of light comprises an infrared spectrum.

6. The system of claim 5, wherein the light source is configured to illuminate at about 1300 nm.

7. The system of claim 5, wherein the light source is configured to illuminate at about 1550 nm.

8. The system of claim 1, wherein the light source comprises a broadband source.

9. An iris imaging system, comprising:
   at least one light source configured to illuminate an iris at a spectrum of light greater than about 1100 nm; and
   at least one image capturing device comprising a detector, the device configured to:
   capture an image of the iris via light reflected from the iris at the spectrum greater than about 1100 nanometers; and
   provide a signal representing one or more features of the iris in response to the light reflected from the iris.

10. The system of claim 9, comprising a controller configured to control movement of the image capturing device.

11. The system of claim 9, comprising a processor configured to:
    localize the iris using features of the iris;
    compare the features with a database of iris patterns; and
    recognize the iris based upon the comparison.

12. The system of claim 9, wherein the light source comprises a broadband light source.

13. The system of claim 9, wherein the light source is configured to illuminate at about 1300 nm.

14. The system of claim 9, wherein the light source is configured to illuminate at about 1550 nm.

15. The system of claim 9, wherein the at least one image capturing device is configured to capture an image of the iris at a bandwidth in a range between about 1300 nm and about 1550 nm.

16. The system of claim 9, wherein the detector comprises indium-gallium-arsenide.

17. The system of claim 1, wherein the at least one image capturing device comprises a camera.

18. A method of fabricating an iris imaging system, comprising:

providing at least one light source for illuminating an iris with a spectrum of light; and providing an image capturing device comprising at least one of an indium-gallium-arsenide detector, a lead sulphide, and a lead selenide based detector for capturing an image of the iris and for providing a signal representing one or more features of the iris.

19. The method of claim 18, wherein said providing an image capturing device comprises providing one or more fixed or pan-tilt mounts for the image capturing device.

20. The method of claim 18, comprising providing a processor configured to:

localize the iris using features of the iris;

compare the features with a database of iris patterns; and recognize the iris based upon the comparison.

21. A method of fabricating an iris imaging system, comprising:

providing at least one light source for illuminating an iris with a spectrum of light; and providing an image capturing device configured to illuminate the iris at a spectrum of light greater than about 1100 nm for capturing an image of the iris and for providing a signal representing one or more features of the iris.

22. The method of claim 21, wherein said providing an image capturing device comprises providing one or more fixed or pan-tilt mounts for the image capturing device.

23. The method of claim 21, comprising providing a processor configured to:

localize the iris using features of the iris;

compare the features with a database of iris patterns; and recognize the iris based upon the comparison.

* * * * *